(12) United States Patent
Chambon et al.

(10) Patent No.: US 8,269,173 B2
(45) Date of Patent: Sep. 18, 2012

(54) CELL, DEVICE COMPRISING THIS CELL AND METHOD FOR MEASURING THE AMOUNT OF INSOLUBLE PARTICLES IN A FLUID AND APPLICATIONS

(75) Inventors: Cécile Chambon, Chaponost (FR); André Diot, Fleurier (CH); Frédéric Jose, Estrablin (FR); Leire Oro-Urrea, Lyons (FR)

(73) Assignee: Total Raffinage Marketing, Puteaux (FR)

( * ) Notice: Subject to any disclaimer, the term of this patent is extended or adjusted under 35 U.S.C. 154(b) by 199 days.

(21) Appl. No.: 12/666,527

(22) PCT Filed: Jun. 25, 2008

(86) PCT No.: PCT/FR2008/000897
§ 371 (c)(1),
(2), (4) Date: Dec. 23, 2009

(87) PCT Pub. No.: WO2009/016282
PCT Pub. Date: Feb. 5, 2009

(65) Prior Publication Data
US 2010/0182591 A1    Jul. 22, 2010

(30) Foreign Application Priority Data
Jun. 26, 2007  (FR) ...................................... 07 04588

(51) Int. Cl.
*G01J 5/02* (2006.01)
(52) U.S. Cl. ................... 250/339.11; 250/341.8; 356/38
(58) Field of Classification Search ............... 250/341.8, 250/339.11; 356/38
See application file for complete search history.

(56) References Cited

U.S. PATENT DOCUMENTS

| | | | |
|---|---|---|---|
| 2,845,388 A | * | 7/1958 | Weisgerber et al. ..... 204/157.15 |
| 3,452,586 A | | 7/1969 | Childs et al. |
| 4,940,900 A | * | 7/1990 | Lambert ....................... 250/343 |
| 5,239,258 A | | 8/1993 | Kauffman |
| 5,287,731 A | | 2/1994 | Florkowski et al. |
| 5,715,046 A | | 2/1998 | Tolvanen et al. |
| 6,690,452 B2 | * | 2/2004 | Wilks, Jr. ......................... 356/70 |
| 7,582,874 B2 | | 9/2009 | Reminiac et al. |
| 7,889,337 B2 | * | 2/2011 | Al-Jaroudi et al. ........... 356/338 |

FOREIGN PATENT DOCUMENTS

| | | |
|---|---|---|
| DE | 970 735 | 10/1958 |
| DE | 1 911 656 | 3/1965 |
| DE | 24 18 637 | 10/1975 |
| DE | 43 12 112 | 10/1994 |

(Continued)

*Primary Examiner* — Christine Sung
(74) *Attorney, Agent, or Firm* — Harness, Dickey & Pierce, P.L.C.

(57) ABSTRACT

The disclosure relates to a cell for measuring the amount of insoluble particles in a fluid that comprises a duct that passes through the cell, a filter for the particles contained in the fluid, the filter being positioned in the duct, an emitter capable of emitting an electromagnetic beam directed towards the insoluble particles concentrated on the filter, and a receiver capable of receiving the electromagnetic beam emitted by the emitter and reflected by the insoluble particles concentrated on the filter. The disclosure also relates to a device comprising this cell, to a method for measuring the amount of insoluble particles in a fluid and to applications thereof, in particular to the study of the oxidation stability of petroleum distillates, to the antioxidant capacity of additives of petroleum products and to the determination of the asphaltene content of petroleum products.

12 Claims, 3 Drawing Sheets

FOREIGN PATENT DOCUMENTS

| | | |
|---|---|---|
| EP | 1 775 571 | 4/2007 |
| FR | 2 647 903 | 12/1990 |
| FR | 2 870 598 | 5/2004 |
| FR | 1 751 518 | 2/2007 |

* cited by examiner

CELL, DEVICE COMPRISING THIS CELL AND METHOD FOR MEASURING THE AMOUNT OF INSOLUBLE PARTICLES IN A FLUID AND APPLICATIONS

CROSS-REFERENCE TO RELATED APPLICATIONS

This application is a National Phase Entry of International Application No. PCT/FR2008/000897, filed on Jun. 25, 2008, which claims priority to French Application 07/04588, filed on Jun. 26, 2007, both of which are incorporated by reference herein.

BACKGROUND AND SUMMARY

The present invention relates to a cell for measuring the amount of insoluble particles in a fluid, to a device comprising such cell as well as to a method for measuring the amount of insoluble particles in a fluid. The invention also relates to the application of this method and to the use of the device according to the invention in the study of oxidation stability of oil middle distillates, in the study of the antioxidant capacity of an additive of petroleum products and in the determination of the amount of asphaltenes present in a petroleum product sample.

Conventionally, oil middle distillates are oil distillates which have a boiling point substantially above 175° C. and which are 90% vaporized at a temperature below 370° C. Kerosine, gasoil or domestic fuel oil (DFO) notably belong to these oil middle distillates. In order to determine the storage stability of these fluids, the standardization bodies, ASTM for the United States and AFNOR for France, have respectively defined under references ASTM D 2274 and NF EN ISO 12205 (classification index NF M07-047), an oxidation stability test for middle oil distillates. This test in a first step consists of filtering a fluid sample so as to determine the amount of insoluble particles, called "existing insolubles", actually present in this state in the fluid.

In a second phase, the fluid sample is placed in an oxidation cell. In this cell, the fluid is heated to a temperature of 95° C. for 16 hours. At the same time, oxygen gas is injected into the sample continuously. After having been cooled, the fluid sample is poured on a filter so as to retain the non-soluble particles then present in the fluid, these particles being called in the NF standard "filterable insolubles". The amount of filterable insolubles is finally determined by weighing the residue present on the filter.

In a third step, the oxidation cell is rinsed by means of a trisolvent—usually consisting of toluene, methanol and acetone. The trisolvent is then evaporated. The residue obtained after this evaporation consists of non-soluble particles called in the NF standard "adherent insolubles". The amount of adherent insolubles is determined by weighing the mass of the residue after evaporation of the trisolvent. The total amount of insoluble particles or "total insolubles" allows determination of whether the tested liquid has satisfactory stability towards oxidation. This amount of total insolubles is obtained by adding the amounts of filterable insolubles and adherent insolubles.

Although actually allowing determination of the stability towards oxidation of middle oil distillates, this test has the drawback of being long, complicated, requiring a significant volume of sample (generally 350 mL) and having poor repeatability. Further, significant operator time (of the order of 3 h) is required for applying this method and a large amount of organic solvent is notably handled for proceeding with the cleaning of the required glassware. Further, with the known method, it is not possible to obtain information concerning the kinetics for formation of the insoluble particles.

From EP 1 751 518 in the name of the applicant, a device is known for measuring light in a liquid by inserting into the liquid at least one probe operating by indirect transmission—reflection—of the light in the fluid. EP 1 751 518 also describes a method for measuring, by means of the measuring device, the flocculation threshold of a colloidal medium by staged addition of apolar solvent, a drop in the transmitted light in the measuring device expressing occurrence of flocculation. However, in the state in the art, there are no available means for automating the oxidation stability test of oil middle distillates, as presented above, nor for reducing the operator time or the use of organic solvent.

Moreover, DE-A-43 12 112 discloses a device for measuring the soot concentration of flue gases. This device comprises a probe provided at one end with a measuring component containing a housing. This housing is intended for receiving a filter for measuring soots, when the measuring component is in its measuring position. The measuring component also comprises, in the area of the housing, an optical measuring device for determining the amount of soot. This optical measuring device may emit a light intensity and measure the light reflected by the measuring filter.

EP-A-1 775 571 teaches a device for monitoring the particle burden of a fluid. The monitoring device includes a measuring chamber with an inlet and outlet for the fluid. A filter is placed in the measuring chamber, between the inlet and the outlet, for filtering the particles. An illumination device is positioned in the measuring chamber for illuminating the filter. An image recording device is also positioned in the measuring chamber for capturing images of the filter.

DE-A-19 11 656 describes a device for monitoring the ageing of oil for conveying heat in a circuit. The device comprises a straight conduit inside which a filter is positioned. The filter is positioned so as to be crossed by the oil. A light source is arranged on the inlet side of the straight conduit. The light source emits light which crosses the filter. A photovoltaic cell is arranged on the outlet side of the straight conduit. A measuring apparatus is connected to the photovoltaic cell in order to determine the extinction level of the light beam which has crossed the filter. Finally, U.S. Pat. No. 5,715,046 teaches a method and a device for determining the stability of an oil by measuring the light intensity reflected by the surface of the oil when an asphaltene-based liquid flocculant is added to the oil.

The object of the present invention is to provide a device and a measurement method which at least partly overcomes the aforementioned drawbacks. More particularly, the invention is directed to providing a measurement device capable of automatically determining the amount of insoluble particles in a tested liquid. The invention is also directed to providing a measuring cell adapted so as to be applied in the device according to the invention, the measuring cell allowing determination of the amount of insolubles in the tested liquid.

The present invention proposes a cell for measuring the amount of insoluble particles in a fluid comprising:
 a duct passing through the cell,
 a filter intended for retaining the particles contained in the fluid, the filter being positioned in the duct,
 an emitter adapted for emitting an electromagnetic beam directed towards the insoluble particles concentrated on the filter, and a receiver adapted for receiving the electromagnetic beam emitted by the emitter (52) and reflected by the insoluble particles concentrated on the filter.

According to embodiments of the invention, the measuring cell comprises one or more of the following optional features, taken alone or as a combination:
- the electromagnetic beam is a light beam selected from the group comprising an infrared beam, a near infrared beam or an ultraviolet beam;
- the emitter is formed by at least one light-emitting diode;
- the receiver is selected from the group comprising a light emitting diode and a photodiode;
- the filter is made in a material selected from the group comprising polymer-based plastic material such as nylon, nitrocellulose and glass fiber;
- the filter has a porosity comprised between 0.1 and 2 μm and preferably between 0.5 and 1.5 μm;
- the measuring cell comprises a sensor for measuring the temperature of the fluid;
- the measuring cell comprises screen-forming means positioned on the direct path, between the emitter and the receiver, of the electromagnetic beam; and
- the incident beam forms with an axis perpendicular to the filter an angle comprised between 45 and 80° and preferably between 60 and 80°.

The invention also relates to a device for measuring the amount of insoluble particles in a fluid including:
- a measuring cell according to the invention as described hereinbefore in all its combinations,
- a container adapted for containing a fluid sample to be tested, a circuit for circulating the fluid between the container and the measuring cell, and
- means for circulating the fluid in the circuit.

According to embodiments of the invention, the measuring device comprises one or more of the following optional features, taken alone or as a combination:
- the measuring device comprises a duct for injecting gas into the sample;
- the device further comprises means for heating the sample;
- the device comprises a sensor for measuring the temperature of the sample;
- the device comprises a heat exchanger between a section of the circuit located upstream from the measuring cell and a section of the circuit located downstream from the measuring cell;
- the device comprises a sensor for measuring the fluid flow rate in the circuit;
- the device comprises a pressure sensor located upstream from the measuring cell; and
- the measuring device further comprises a computer adapted for receiving information from the emitter and/or the receiver and/or the temperature sensor of the cell and/or the temperature sensor of the sample and more generally from any system for physical measurements positioned in the device, for sending as a response control signals to the different constituents of the device, such as the means for circulating the fluids, and/or for example to the emitter and/or to a display device.

The invention also relates to a method for measuring the amount of insoluble particles in a fluid comprising at least the following steps of:
- concentrating the insoluble particles by filtering the fluid;
- determining the amount of the particles from the measurement of the absorption of electromagnetic radiation by the concentrated particles, the measurement of the absorption being conducted by comparing electromagnetic radiation incident on the concentrated particles and the electromagnetic radiation reflected by the concentrated particles.

According to alternatives of the invention, the measuring method includes one or more of the following optional features, taken alone or as a combination:
- the fluid is continuously circulated between a container and a filter adapted for filtering the insoluble particles;
- gas is injected into the fluid contained in the container;
- the injected gas is oxygen;
- the determination of the amount of the particles is conducted continuously;
- the fluid contained in the container is heated;
- the intensity of the emitted electromagnetic radiation is maintained constant; and
- the intensity of the reflected electromagnetic radiation is maintained constant.

The invention also relates to the use of the measuring cell according to the invention or of the measuring device according to the invention for measuring the oxidation stability of oil middle distillates by determining the amounts of insolubles contained in the distillate. The invention also relates to the application of the measuring method according to the invention to the measurement of the oxidation stability of middle oil distillates by determining the amounts of insolubles contained in the distillate. The invention also relates to the use of the measuring cell according to the invention or of the measuring device according to the invention for determining the amount of asphaltenes present in a petroleum product sample.

The invention further concerns the application of the method according to the invention to the determination of the amount of asphaltenes present in a petroleum product sample. The invention also relates to the use of the measuring cell according to the invention or of the measuring device according to the invention for measuring the antioxidant capacity of petroleum product additives. The invention finally concerns the application of the measuring method according to the invention to measuring the antioxidant capacity of petroleum product additives.

BRIEF DESCRIPTION OF DRAWINGS

Other features and advantages of the invention will become apparent upon reading the description which follows of a preferred embodiment of the invention, given as an example and with reference to the appended drawing, wherein.

DETAILED DESCRIPTION

Figure 1:
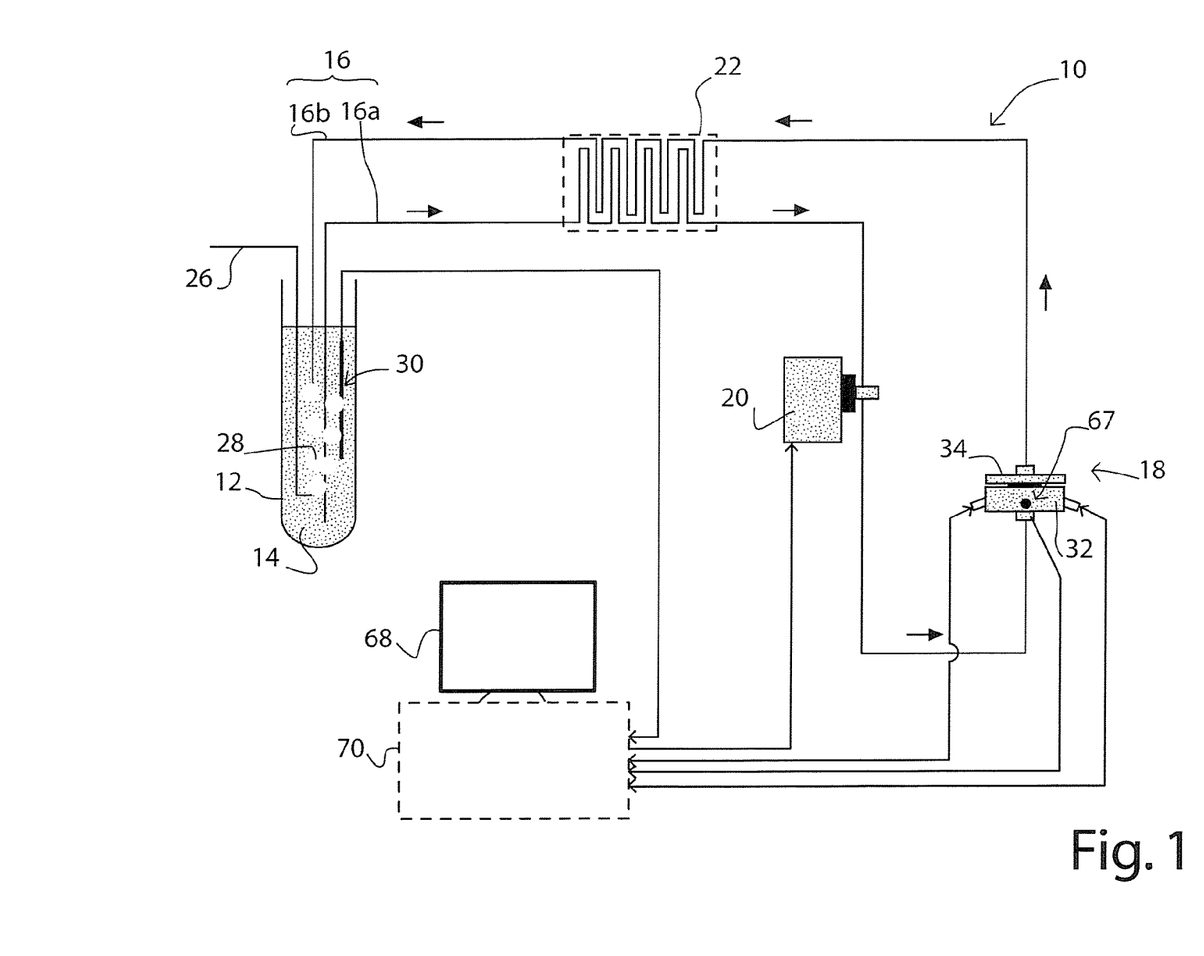
FIG. 1 illustrates a diagram of a measuring device according to the invention.

According to the invention, the device 10 for measuring insoluble particles in a fluid comprises a container 12 containing the fluid sample 14 to be tested—in this case a middle oil distillate—a circuit 16 for circulating the fluid, a cell 18 for measuring the insoluble particles in the fluid, positioned on the circuit 16 of the fluid and means 20 for circulating the fluid in the circuit 16. The circulating means 20 notably include a peristaltic pump (or a pump with a rotary piston) with which a constant fluid flow rate may be ensured in the circuit 16. Other means for circulating the fluid may however be applied such as a suction device.

Optionally, the measuring device 10 further includes a device 22 for cooling the fluid positioned between the container 12 and the measuring cell 18. The cooling device is a heat exchanger 22 positioned between a section 16a of the circuit 16 located upstream from the measuring cell 18 and a section 16b of the circuit 16 located downstream from the cell 18. More specifically, the heat exchanger 22 here consists of two grooved aluminum plates with protection of the metal by sprayed Teflon. Of course, other cooling devices may be applied here such as for example a cooling unit or a Peltier effect cooler.

The container 12 is associated here with means (not shown) for heating the sample 14 to be tested, contained in the container 12, as well as with a duct 26 for injecting gas 28, notably oxygen, immersed in the sample 14. Here, the heating means consist of a heat-controlled oil bath with a volume of 5 L, but of course other heating means may be applied in the device 10 according to the invention. The injection duct 26 is for example made in the form of a ball flow meter.

Optionally, a temperature sensor 30 is also provided in order to measure the temperature of the sample 14. In accordance with the embodiment of the device according to the invention illustrated in FIG. 1, this sensor 30 is immersed in the sample 14. Optionally, the device 10 according to the invention may also include a butterfly valve (not shown) or any other means for measuring the fluid flow rate in the circuit 16. Also optionally, the device 10 according to the invention may include a pressure sensor (not shown) located upstream from the measuring cell.

Figure 2:
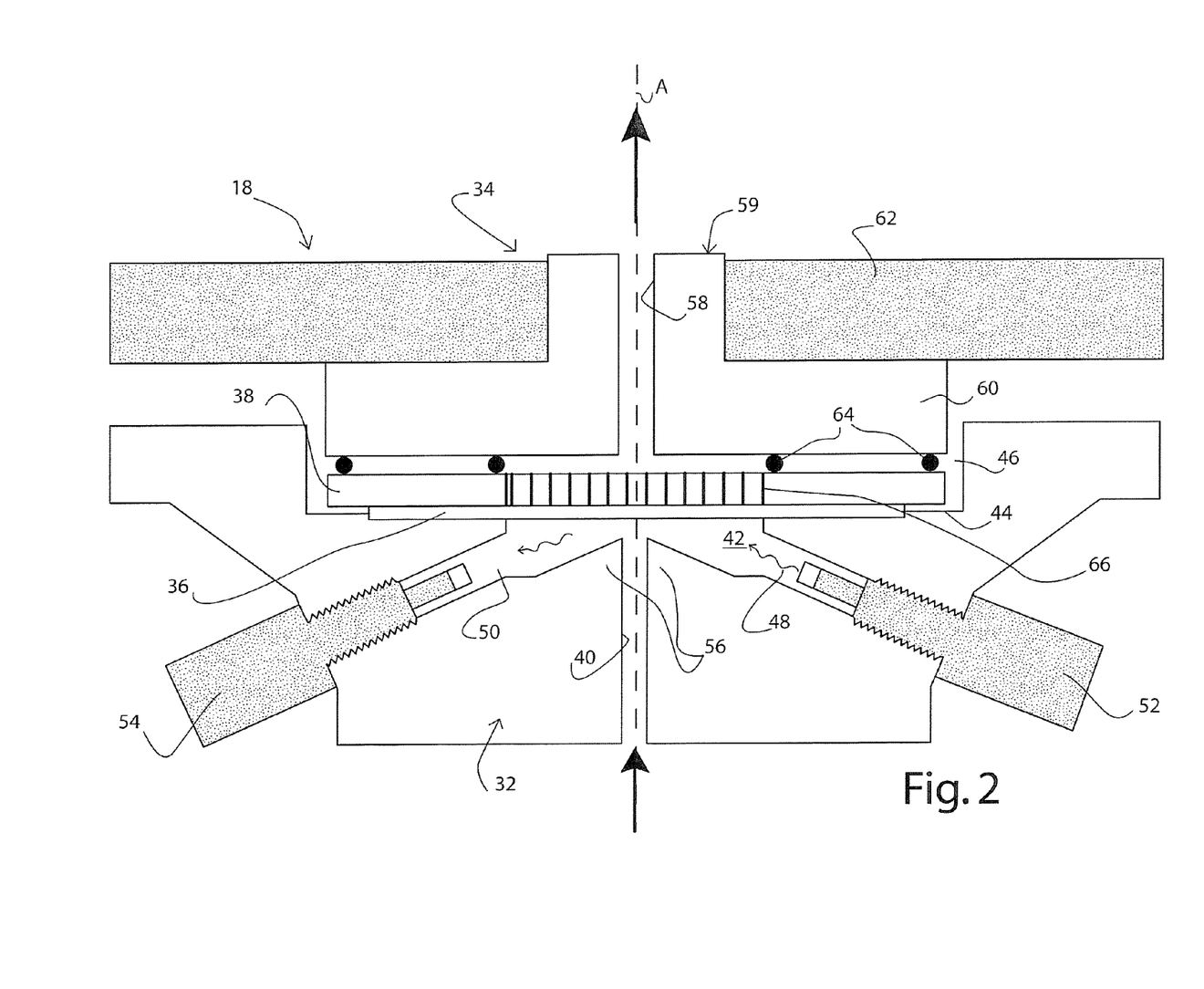
FIG. 2 illustrates a diagram of a measuring cell according to the invention applied in the device of FIG. 1.

As this is illustrated in FIG. 2, the measuring cell 18 includes a base 32 and a head 34 which clasp a support 36 for concentrating the particles contained in the fluid—in this case a filter—positioned on a supporting part 38. In the illustrated embodiment, the filter 36 is in nylon and has a porosity of 0.8 µm. However, according to other applications, the filter 36 may also be made in different plastic materials based on polymers, or in nitrocellulose or in glass fiber and have a porosity comprised between 0.1 and 2 µm and preferably between 0.5 and 1.5 µm.

The base 32 of the measuring cell 18 is crossed by a duct 40 preferably arranged along the middle axis A of the base 32. This duct 40 opens out at a cavity 42 formed in the base surface 44 of a recess 46 made in the base 32. The recess 46 is adapted for receiving the filter 36 and the filter support 38.

Two opening holes 48, 50 are made in the base 32 so as to also open into the cavity 42. These opening holes are in the plane of FIG. 2, substantially symmetrical relatively to the axis A of the base 32. An electromagnetic emitter 52 and an electromagnetic receiver 54 are mounted notably screwed on—inside these opening holes 48, 50 so that the electromagnetic emitter 52 and the electromagnetic receiver 54 are each oriented towards the cavity 42 and more specifically in the direction of the portion of the filter 36 which is flush with the cavity 42. In this case, the electromagnetic emitter 52 is a light emitter and the electromagnetic receiver 54 is a light receiver.

Optionally, as this is illustrated in FIG. 2, the base 32 of the measuring cell 18 has screen-forming means 56 which are interposed between the emitter 52 and the receiver 54 in order to prevent direct reception—i.e. without any prior reflection—by the receiver 54 of radiation emitted by the emitter 52. According to the illustrated embodiment, these screen-forming means 56 are made in a single piece with the base 32, which has a protruding portion 56 in the cavity 42. However, other alternative embodiments of these screen-forming means 56 may be contemplated, such as attachment by screwing of an added part.

According to the illustrated embodiment, the emitter 52 and the receiver 54 consist of at least one light-emitting diode (LED), the emitted beam being an infrared beam. However, according to an alternative, the receiver 54 may also consist of at least one photodiode. Also, the beam may, according to other alternatives, be a near infrared beam or further an ultraviolet beam.

According to the illustrated embodiment, the base 32 of the measuring cell 18 is in a rigid material having very good resistance to solvents, for example a plastic material such as polyoxymethylene. The head 34 of the measuring cell 18 is also crossed by a duct 58 arranged along the middle axis A of the head 34 which is the middle axis of the head 34, of the base 32 and of the measuring cell 18 when the measuring cell 18 is mounted. Thus, the duct 58 is arranged so as to be substantially facing the duct 40 arranged in the base 32 when the base 32 and the head 34 are assembled with each other. The head 34 has a central part 59 notably having a portion 60 adapted for being at least partly inserted into the recess 46 arranged in the base 32. With this portion 60 it is thereby possible to facilitate centering of the ducts 40 and 58 on the one hand, and the mounting of the head 34 on the base 32 on the other hand.

The head 34 moreover has a strengthening part 62 integral with the central part 59. In this case, the strengthening part 62 is metal while the central part is in a rigid material as indicated above. Optionally, O-ring gaskets 64 are positioned between the portion 60 of the head 34 of the cell 18 and the support 38 of the filter 36 in order to ensure the seal of the measuring cell 18. In this case, the filter support 38 includes a central area 66 in a sintered material which allows the filter 36 to be supported on the one hand, while letting the fluid flow through the filter support 38.

According to the embodiment illustrated in FIG. 2, the filter 36 is positioned substantially perpendicularly to the ducts 40, 58 respectively arranged in the base 32 and the head 34 of the measuring cell 18, so that all the fluid flowing into these ducts 40, 58 is efficiently filtered by the filter 36. As illustrated in FIG. 1, the measuring cell 18 may optionally be completed with a sensor 67 for measuring the temperature of the fluid flowing through the cell.

According to the illustrated embodiment, the measuring device 10 includes an electronic control and analysis unit 68—in this case a computer—which is capable of communicating via an interface 70 with the different components making up the measuring device 18. Thus, the computer 68 may receive the following pieces of information:

the temperature of the sample 14 as measured by the sensor 30,
the temperature of the fluid passing through the measuring cell 18 as measured by the sensor 67,
the intensity of the beam emitted by the emitter 52 or "emitted intensity",
the intensity of the beam received by the receiver 54 or "received intensity", and
the fluid flow rate in the circuit 16, this flow rate being measured by a suitable sensor (not shown) such as a butterfly valve, for example.

Subsequently, the computer 68 may control:
the intensity of the beam emitted by the emitter 52, so as for example to maintain the received intensity constant,
the fluid flow rate in the circuit 16 by controlling the pump 20, and
the means for heating the sample (not shown) so as to maintain the temperature of the sample 14 constant or on the contrary change it.

The measuring device 10 may also include a device of the flatbed plotter type (not shown) so as to view in real time the time course of the concentration of insoluble particles on the filter 36. To do this, the device of the flatbed plotter type may be connected to the computer 68, optionally via the interface 70. However, according to an alternative of the invention, the computer 68 may also display directly and in real time the time course of the signal, representative of the concentration of insoluble particles on the filter 36.

The operation of the measuring device 10 and of the measuring cell 18 according to the invention directly ensues from the structural description which has just been given. This operation is described subsequently in the non-limiting case of an oxidation test of a DFO sample. The operating mode of the measuring cell is first of all described, with reference to FIG. 2.

The emitter 52 emits a light beam which, in the absence of concentrated particles on the filter 36, is almost totally reflected by the filter 36. To do this, the filter 36 is made in a material—in this case nylon—which reflects a large portion of the incident beam—notably infrared polychromatic radiation here. As, by design, the emitter 52 and the receiver 54 are symmetrical relatively to the axis A of the measuring cell 18, the beam is reflected towards the receiver 54 which receives a beam, the intensity of which is substantially equal to the intensity of the emitted beam.

When the DFO flows through the ducts 40, 58, the insoluble particles present in this DFO are concentrated by the filter 36. Thus, the insoluble particles present in the DFO and which have a diameter greater than the porosity of the filter 36, agglomerate on the filter 36 and form a filtration cake. Accordingly, the beam emitted by the emitter 52 is partly absorbed by these concentrated particles and a smaller portion of the incident beam is reflected towards the receiver 54. Accordingly, the intensity of the beam received by the receiver 54 (or received intensity) decreases. More specifically, the received intensity decreases with the increase in the amount of particles concentrated on the filter 36. By calibrating the measuring cell 18 with fluids, for which the concentration of total insolubles is known, it is subsequently possible to match an absorption value of the intensity of the emitted beam as measured by the measuring cell 18, with a mass or an amount of particles concentrated on the filter 36.

In the case of the measuring cell 18 illustrated in FIG. 2, it is also of interest that the angle of incidence (measured relatively to the axis A of the cell, the axis A being perpendicular to the filter 36) of the emitted beam is large and notably that it is comprised between 45 and 80° and preferably between 60 and 80°. Indeed, for a same diameter of the emitted beam, the larger the incidence angle, the wider is the area of the filter 36 subject to the incident beam. A more accurate measurement results from this since even the particles agglomerated at the peripheral area of the filter 36 may absorb a portion of the incident beam emitted by the emitter 52.

However, direct transmission of the beam emitted from the emitter 52 to the receiver 54 should be avoided. Indeed, such a direct transmission is likely to distort the measurement and therefore make it less accurate. This direct transmission is avoided here by interposing between the emitter 52 and the receiver 54, screen-forming means 56 made as single piece with the base 32 of the measuring cell 18.

In the following, an application of the measuring device 10 is described with reference to FIG. 1. According to this application of the device, the intensity of the beam emitted by the emitter 52 is maintained constant during the whole measurement. In a first phase, a sample 14 of about 50 mL of DFO is placed in the container 12. Thus, a very small volume of liquid to be tested is required for conducting the measurement with the device according to the invention. To do this, the circuit 16 is preferably of reduced length, as small as possible.

In a second phase, the pump 20 is started. Subsequently, the intensity of the received beam first of all drops when the fluid passes through the measurement cell 18. Indeed, when the pump 20 is cut off, no particle is present on the filter 36 which therefore reflects the beam emitted by the emitter 52.

However, when the pump 20 is started, the insoluble particles (designated above as existing insolubles) initially present in the DFO are gradually deposited on the filter 36. These particles absorb a more significant portion of the incident beam emitted by the emitter 52 than the filter 36. Accordingly, as the insoluble particles become concentrated on the filter, the intensity of the beam received by the receiver 54 decreases. Finally, when all the existing insolubles initially present in the fluid are concentrated on the filter 36, the intensity of the received beam stabilizes. A plateau of the intensity received by the receiver 54 is observed which allows determination of the amount of existing insolubles—i.e. insoluble particles initially present in the DFO. Although this determination of the amount of existing insolubles is not required in the ASTM D2274 standard, one skilled in the art will appreciate the additional information obtained by applying the present invention.

In a third phase, the sample 14, contained in the container 12, is heated by means of the heat-controlled oil bath, in this case at a temperature of 95° C. Oxygen is injected at the same time into the sample 14. It is then possible to observe the time course of the received intensity during the whole period for heating and oxidizing the sample, which may for example be 16 hours. Considering that the measuring unit 18 behaves identically for the existing gums and for the potential gums, it is possible to determine the kinetics for formation of potential gums.

As this has been described, the measuring device 10 allows application of a method for measuring the amount of insoluble particles in a fluid, the basic steps of which are the following:

a) concentrating the insoluble particles;
b) determining the amount of particles by measuring the absorption of electromagnetic radiation—in this case light radiation—by the concentrated particles.

And, as described hereinbefore, in accordance with an alternative of the measuring method according to the invention, measurement of the absorption is conducted by comparing the respective intensities of light radiation incident on the concentrated particles and of light radiation reflected by the concentrated particles.

Of course, the present invention is not limited to the examples and to the embodiments as described and illustrated, but it is capable of many alternatives accessible to one skilled in the art. Thus, notably, the device may be applied for many measurements of amounts of insoluble particles, or made insoluble beforehand, present in a liquid (with or without sparging, with or without heating the liquid). In particular, the measuring cell, the measuring device and the measuring method find a particularly interesting application in the measurement of the antioxidant capacity of petroleum product additives.

Indeed, because the amount of insoluble particles may be viewed at any instant, it is possible to add at any instant of the measurement an antioxidant additive in the fluid sample to be tested. After adding this additive, it is possible to view the amount of insoluble particles accumulated on the filter. Alternatively, it is possible to compare the change over time and/or the amount of filterable insolubles on the filter for a same distillate, with and without additive. It is therefore possible to determine in this way the antioxidant effect of this additive on the sample.

Another interesting application of the measuring cell, or the measuring device and of the measuring method according to the invention, lies in the determination of the amount of asphaltenes present in a petroleum product sample. To do this, staged addition of apolar solvent in a colloidal fluid to be tested is performed until total flocculation of the asphaltenes. This total flocculation causes concentration of the asphaltenes on the filter, in the same way as for the insoluble particles mentioned above, and therefore a peak of absorption of the emitted light beam which may be quantified in terms of asphaltene concentration. The petroleum products for which it is desired to measure the asphaltene content, are notably the black products. A complete description of these black products and of the addition technique (notably of the apolar solvent) for causing precipitation is found in document EP 1 751 518 in the name of the applicant, to which reference is made for more details.

Moreover, the measure described hereinbefore was conducted while retaining a constant emitted intensity. It was seen that this operating mode has the advantage that the measurement is linear, i.e. the received signal linearly depends on the amount of insolubles present on the filter. However, it was seen that the operating mode aiming at maintaining the received intensity constant has larger sensitivity. Finally, although the application of the device was described in the case of a DFO, it may be applied to many other liquids and notably to middle oil distillates, or other petroleum products in a general way.

The following examples illustrate the invention without limiting it. A study of the sensitivity of the measurements conducted according to the invention is first of all mentioned. For this study, the sample used is DFO no. 21101.

TABLE 1

Results of the measurements of the amount of insolubles present in DFO no. 21101, conducted according to the ASTM D 2274 standard

| Filtered volumes (mL) | Test no. 1 Measured insolubles (mg) | Test no. 2 Measured insolubles (mg) |
|---|---|---|
| 25 | 0.00 | 0.06 |
| 50 | 0.00 | 0.02 |
| 100 | 0.09 | 0.02 |
| 150 | 0.06 | 0.02 |
| 200 | 0.10 | 0.39 |

TABLE 2

Results of the measurements of the amount of insolubles present in DFO no. 21101, conducted according to the invention

| Filtered volumes (mL) | Measured insolubles (mg) |
|---|---|
| 25 | 0.05 |
| 50 | 0.09 |
| 75 | 0.12 |
| 100 | 0.16 |
| 125 | 0.19 |
| 150 | 0.22 |

Figure 3:
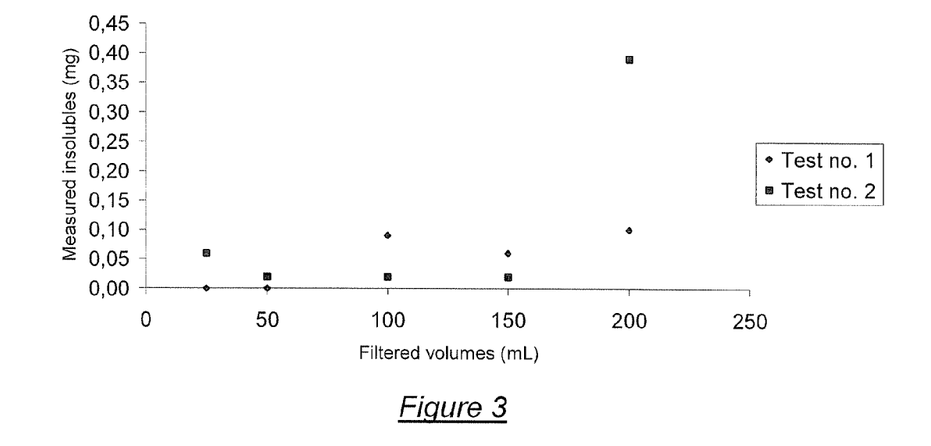
FIGS. 3 and 4 illustrate the results of measurements of the amount of insolubles present in DFO no. 21101, depending on the volume of the tested sample, the measurement having been respectively conducted according to the ASTM D 2274 standard and according to the method in accordance with the invention.
Figure 4:
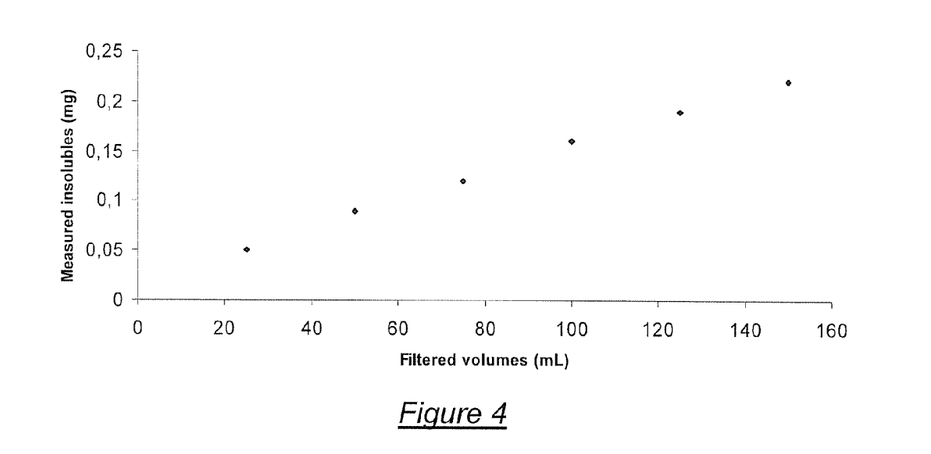

FIGS. 3 and 4 graphically illustrate the results of these measurements.

Thus, it appears that the measurements with the ASTM D 2274 standardized method have large dispersion. Further, these results contradict the expected results according to which the amount of insolubles varies linearly with the amount of DFO no. 21101 making up the sample. Indeed, the amount of insolubles and the volume of the sample are related through a proportionality relationship, the proportionality coefficient being by definition equal to the concentration of insolubles. Thus, the ASTM D 2274 measuring method seems to have relative inaccuracy. On the contrary, the results of Table 2, illustrated in FIG. 4, actually express the linearity relationship between the measured amount of insolubles and the volume of DFO no. 2201 making up the sample. Thus, with the measuring method according to the invention it is possible to obtain results which appear more consistent.

A study of the repeatability of the measurements conducted according to the invention is mentioned subsequently. For this study, the sample used is DFO no. 21100. The repeatability is defined as the value below which is located, with a specified probability, the absolute value of the difference between two individual results obtained under identical conditions, i.e. with the same operator, the same apparatuses, the same laboratory and within a short time interval. The selected probability is 95%.

It is recalled that the general formula of the repeatability of a measurement is given by the formula:

$$r = t(m-1, 0.95) \times \sqrt{2} \times \sigma \quad (1)$$

wherein:
r is the repeatability of the formula;
m is the number of conducted identical measurements;
t (m−1, 0.95) is the Student factor t at a confidence level of 95%; with m−1 degrees of freedom; and
σ is the standard deviation of the measurements.

TABLE 3

Repeatability of the measurement of the amount of insolubles present in DFO no. 21100, conducted according to the ASTM D 2274 standard

| Tests | Measured total insolubles (g/m$^3$) |
|---|---|
| 1 | 5.00 |
| 2 | 5.40 |
| Average | 5.20 |
| Standard deviation | 0.28 |
| Repeatability | 5.08 |

TABLE 4

Repeatability of the measurement of the amount of insolubles present in the DFO no. 21100, conducted according to the invention

| Tests | Measured insolubles (g/m$^3$) |
|---|---|
| 1 | 9.20 |
| 2 | 9.30 |
| 3 | 9.50 |
| 4 | 9.60 |
| 5 | 9.70 |
| 6 | 9.00 |
| 7 | 9.20 |
| Average | 9.36 |
| Standard deviation | 0.25 |
| Repeatability | 0.87 |

In order to calculate the repeatabilities, the following values were used:
t(1, 0.95)=12.71, and
t(6, 0.95)=2.45.

According to the results of the conducted measurements, the repeatability of the method according to the invention is clearly smaller than the repeatability of the method according to the ASTM D 2274 standard. With the application of the present invention it is therefore possible, as compared with the methods of the ASTM D 2274 and NF EN ISO 12205 standards:

to use smaller amounts of samples and of organic solvent;
to obtain a result within the shortest possible time;
to obtain better repeatability and therefore better reliability on this result; and
to have a measuring method which may be automated on line in a manufacturing process, for example for middle oil distillate.

The invention claimed is:

1. A method for measuring the oxidation stability of oil middle distillates by determining the amounts of total insolubles contained in the distillate, comprising at least the following steps:
   a) injecting oxygen into the distillate;
   b) concentrating the insoluble particles by filtering the distillate; and
   c) determining the amount of the particles by measuring the absorption of electromagnetic radiation by the concentrated particles, the measurement of the absorption being conducted by comparing electromagnetic radiation incident on the concentrated particles and electromagnetic radiation reflected by the concentrated particles,
the distillate being continuously circulated between a container and a filter adapted for filtering the insoluble particles.

2. The method according to claim 1, wherein the oxygen is injected into the distillate contained in the container.

3. The method according to claim 1, wherein the determination of the amount of the particles is carried continuously.

4. The method according to claim 1, wherein the intensity of the emitted electromagnetic radiation is maintained constant.

5. The method according to claim 1, wherein the intensity of the reflected electromagnetic radiation is maintained constant.

6. The method according to claim 1, wherein the oxygen is injected into the distillate contained in the container and the determination of the amount of the particles is carried continuously.

7. A method for measuring the oxidation stability of oil middle distillates by determining the amounts of total insolubles contained in the distillate, comprising at least the following steps:
   (a) injecting the oxygen into the disllate;
   (b) concentrating the insoluble particles by filtering the distillate; and
   (c) determining the amount of the particles by measuring the absorption of electromagnetic radiation by the concentrated particles, the measurement of the absorption being conducted by comparing electromagnetic radiation incident on the concentrated particles and electromagnetic radiation reflected by the concentrated particles,
the distillate being continuously circulated between a container and a filter adapted for filtering the insoluble particles, wherein the method is applied by a device for measuring the amount of insoluble particles in a fluid including:
   a cell for measuring the amount of insoluble particles in a fluid comprising
      a duct passing through the cell,
      a filter for the particles contained in the fluid, the filter being positioned in the duct,
      an emitter adapted for emitting an electromagnetic beam directed towards the insoluble particles concentrated on the filter, and
      a receiver adapted for receiving the electromagnetic beam emitted by the emitter and reflected by the insoluble particles concentrated on the filter,
   a container adapted for containing a fluid sample to be tested,
   a circuit for circulating the fluid between the container and the measuring cell,
   a pump for circulating the fluid in the circuit, and
   a duct for injecting gas into the sample.

8. The method according to claim 7, wherein the oxygen is injected into the distillate contained in the container.

9. The method according to claim 7, wherein the determination of the amount of the particles is carried continuously.

10. The method according to claim 7, wherein the oxygen is injected into the distillate contained in the container and the determination of the amount of the particles is carried continuously.

11. The method according to claim 7, wherein the intensity of the emitted electromagnetic radiation is maintained constant.

12. The method according to claim 7, wherein the intensity of the reflected electromagnetic radiation is maintained constant.

* * * * *